United States Patent [19]

Drabek et al.

[11] Patent Number: 4,497,746
[45] Date of Patent: Feb. 5, 1985

[54] BENZAMIDOSULFENYLCARBAMOYL HALIDES

[75] Inventors: Jozef Drabek, Oberwil, Switzerland; Manfred Böger, Weil am Rhein, Fed. Rep. of Germany

[73] Assignee: Ciba-Geigy Corporation, Ardsley, N.Y.

[21] Appl. No.: 422,332

[22] Filed: Sep. 23, 1982

Related U.S. Application Data

[62] Division of Ser. No. 305,306, Sep. 24, 1981, Pat. No. 4,413,008.

[30] Foreign Application Priority Data

Oct. 2, 1980 [CH] Switzerland ............... 7362/80
Jun. 2, 1981 [CH] Switzerland ............... 3597/81

[51] Int. Cl.³ .............................................. C07C 83/10
[52] U.S. Cl. ........................ 260/544 C; 260/453 RW
[58] Field of Search ............... 260/453 RW, 544 C; 424/298

[56] References Cited

U.S. PATENT DOCUMENTS 3,047,625 7/1962 Gauss et al. ............... 260/453 RW

FOREIGN PATENT DOCUMENTS 1080738 7/1980 Canada ............... 260/453 RW

Primary Examiner—Alan L. Rotman
Assistant Examiner—Robert C. Whittenbaugh
Attorney, Agent, or Firm—Frederick H. Rabin

[57] ABSTRACT

N-(Benzamidosulfenyl)-N-methylcarbamates of the formula

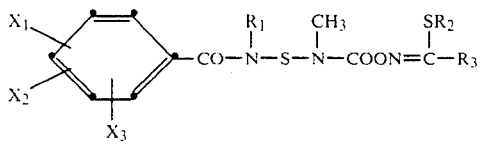

wherein $R_1$ is $C_1$–$C_{10}$ alkyl, $R_2$ is $C_1$–$C_3$ alkyl or allyl, $R_3$ is methyl, —$CONH_2$ or —$CON(CH_3)_2$, and each of $X_1$, $X_2$ and $X_3$ is hydrogen, halogen, $C_1$–$C_4$ alkyl or $C_1$–$C_4$ haloalkyl.

The intermediates for and methods of obtaining these carbamates are disclosed, as is also their use in pest control.

2 Claims, No Drawings

BENZAMIDOSULFENYLCARBAMOYL HALIDES

This is a division of application Ser. No. 305,306 filed Sept. 24, 1981, now U.S. Pat. No. 4,413,008, issued Nov. 1, 1983.

The present invention relates to N-(benzamidosulfenyl)-N-methylcarbamates, to the production thereof, and to the use thereof in pest control.

The N-(benzamidosulfenyl)-N-methylcarbamates of this invention have the formula

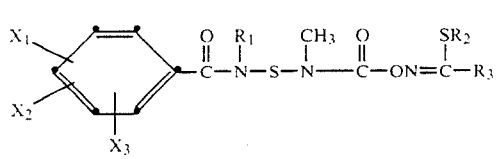

wherein $R_1$ is $C_1$-$C_{10}$alkyl, $R_2$ is $C_1$-$C_3$alkyl or allyl, $R_3$ is methyl, —$CONH_2$ or —$CON(CH_3)_2$, and each of $X_1$, $X_2$ and $X_3$ is hydrogen, halogen, $C_1$-$C_4$alkyl or $C_1$-$C_4$haloalkyl.

Halogen in the above definitions denotes fluorine, chlorine, bromine or iodine, with chlorine being preferred.

The alkyl groups suitable for $R_1$, $R_2$, $X_1$, $X_2$ and $X_3$ can be straight chain or branched. Examples of such groups are: methyl, trifluoromethyl, ethyl, propyl, isopropyl, n-butyl, isobutyl, sec- and tert-butyl, n-pentyl, n-hexyl, n-heptyl, n-octyl, n-nonyl and n-decyl, and the isomers thereof.

Preferred for their activity are compounds of the formula I, wherein $R_1$ is methyl, $R_2$ is $C_1$-$C_3$alkyl, $R_3$ is methyl or —$CON(CH_3)_2$, and each of $X_1$, $X_2$ and $X_3$ is hydrogen, chlorine, methyl or trifluoromethyl.

Particularly preferred, however, are compounds of the formula I, wherein $R_1$ is methyl, $R_2$ is $C_1$-$C_3$alkyl, $R_3$ is methyl or —$CON(CH_3)_2$, each of $X_1$ and $X_2$ is hydrogen, chlorine, methyl or trifluoromethyl, and $X_3$ is hydrogen.

The compounds of formula I can be obtained by methods which are known per se, e.g. as follows:

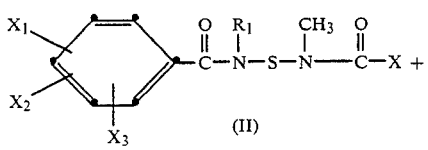

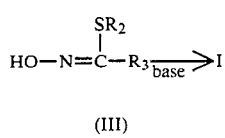

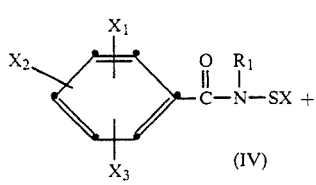

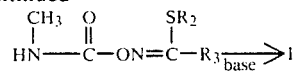

In formulae II to V above, $R_1$, $R_2$, $R_3$, $X_1$, $X_2$ and $X_3$ are as defined for formula I and X is a halogen atom, in particular a fluorine or chlorine atom.

The processes are carried out at a reaction temperature in the range from $-50°$ C. to $+130°$ C., preferably from $-10°$ to $+100°$ C., under normal or slightly elevated pressure and in the presence of a solvent or diluent which is inert to the reactants.

Suitable bases for the processes are, in particular, tertiary amines such as trialkylamines, pyridines and dialkyl anilines, and also hydroxides, oxides, carbonates and bicarbonates of alkali metals and alkaline earth metals, as well as alkali metal alcoholates, e.g. potassium tert-butylate and sodium methylate.

Examples of suitable solvents or diluents are: ethers and ethereal compounds such as diethyl ether, diisopropyl ether, dioxane, tetrahydrofurane; aliphatic and aromatic hydrocarbons, in particular benzene, toluene and xylenes; and ketones such as acetone, methyl ethyl ketone and cyclohexanone.

The starting materials of formula II are novel and also constitute an object of the invention. These compounds can be prepared by methods analogous to those disclosed to those disclosed in European patent application No. 0,010,515 published on Apr. 30th, 1980, and U.S. Pat. No. 4,254,136 issued on Mar. 3rd, 1981. Those of formula III are known and can be prepared by methods analogous to known ones.

The compounds of formula I are suitable for controlling pests of animals and plants. These compounds also possess fungicidal and plant regulating properties.

In particular, the compounds of the formula I are suitable for controlling insects, for example of the orders: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera, and for controlling mites and ticks of the order Acarina.

Most particularly, the compounds of the formula I are suitable for controlling plant-destructive insects, especially plant-destructive feeding insects, in ornamentals and crops of useful plants, especially in cotton plantations (e.g. *Spodoptera littoralis* and *Heliothis virescens*) and in crops of vegetables (for example *Leptinotarsa decemlineata* and *Myzus persicae*).

In this connection it is to be emphasized that the compounds of formula I have both a strongly pronounced systemic as well as contact action against sucking insects, especially sucking insects of the order Homoptera and, most particularly, against insects of the family Aphididae (e.g. *Aphis fabae, Aphis craccivora* and *Myzus persicae*), which can only be controlled with difficulty using known pesticides.

Compounds of formula I also have a very advantageous action against flies, e.g. *Musca domestica,* and against mosquito larvae. In addition, the compounds of formula I have a broad ovicidal and ovilarvicidal action, and they also have a useful action against phytopathogenic nematodes as well as against ectoparasitic mites and ticks e.g. of the families Ixodidae, Argasidae and Dermanyssidae.

The compounds of the formula I are used in unmodified form or, preferably, together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. The methods of application, such as spraying, atomising, dusting, scattering or pouring, are chosen in accordance with the intended objectives and the prevailing circumstances, just like the nature of the compositions.

The formulations, i.e. the compositions or preparations containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethyl formamide, as well as epoxidised vegetable oils such as epoxidised coconut oil or soybean oil; or water.

The solid carriers used e.g. for dusts and dispersible powders, are normally natural mineral fillers, such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are materials such as calcite or sand. In addition, a great number of pregranulated materials or inorganic or organic nature can be used, e.g. especially dolomite or pulverised plant residues.

Depending on the nature of the compound of the formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammoniums salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyoxyethylene adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$–$C_{22}$alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in "McCutcheon's Detergents and Emulsifiers Annual", MC Publishing Corp., Ringwood, N.J., 1979.

The pesticidal formulations usually contain 0.1 to 99%, preferably 0.1 to 95%, of a compound of the formula I, 1 to 99.9% of a solid or liquid adjuvant, and 0 to 25%, preferably 0.1 to 25%, of a surfactant.

Whereas commercial products are preferably formulated as concentrates, the end user will normally employ dilute formulations.

The formulations can also contain further additives such as stabilisers, antifoams, viscosity regulators, binders, adhesives, as well as fertilisers, in order to produce special effects.

FORMULATION EXAMPLES

Formulation Examples for liquid active ingredients of the formula I (throughout, percentages are by weight)

| (1) Emulsifiable concentrates | (a) | (b) | (c) |
|---|---|---|---|
| active ingredient | 20% | 40% | 50% |
| calcium dodecylbenzenesulfonate | 5% | 8% | 5.8% |
| castor oil polyethylene glycol ether (36 moles of ethylene oxide) | 5% | — | — |
| tributylphenol polyethylene glycol ether (30 moles of ethylene oxide) | — | 12% | 4.2% |
| cyclohexanone | — | 15% | 20% |
| xylene mixture | 70% | 25% | 20% |

Emulsions of any required concentration can be produced from such concentrates by dilution with water.

| (2) Solutions | (a) | (b) | (c) | (d) |
|---|---|---|---|---|
| active ingredient | 80% | 10% | 5% | 95% |
| ethylene glycol monomethyl ether | 20% | — | — | — |
| polyethylene glycol 400 | — | 70% | — | — |
| N—methyl-2-pyrrolidone | — | 20% | — | — |
| epoxidised coconut oil | — | — | 1% | 5% |
| petroleum distillate (boiling range (160–190°) | — | — | 94% | — |

These solutions are suitable for application in the form of microdrops.

| (3) Granulates | (a) | (b) |
|---|---|---|
| active ingredient | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| (4) Dusts | (a) | (b) |
|---|---|---|
| active ingredient | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

Formulation examples for solid active ingredients of the formula I (throughout, percentages are by weight)

| (5) Wettable powders | (a) | (b) |
|---|---|---|
| active ingredient | 20% | 60% |
| sodium lignosulfonate | 5% | 5% |
| sodium laurylsulfate | 3% | — |
| sodium diisobutylnaphthalenesulfonate | — | 6% |
| octylphenol polyethylene glycol ether (7–8 moles of ethylene oxide) | — | 2% |
| highly dispersed silicic acid | 5% | 27% |
| kaolin | 67% | — |

The active ingredient is thoroughly mixed with the adjuvants and the mixture is thoroughly ground in a suitable mill, affording wettable powders which can be diluted with water to give suspensions of the desired concentration.

| (6) Emulsifiable concentrate | |
|---|---|
| active ingredient | 10% |
| octylphenol polyethylene glycol ether (4–5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| (7) Dusts | (a) | (b) |
|---|---|---|
| active ingredient | 5% | 8% |
| talcum | 95% | — |
| kaolin | — | 92% |

Dusts which are ready for use are obtained by mixing the active ingredient with the carriers, and grinding the mixture in a suitable mill.

| (8) Extruder granulate | |
|---|---|
| active ingredient | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| (9) Coated granulate | |
|---|---|
| active ingredient | 3% |
| polyethylene glycol 200 | 3% |
| kaolin | 94% |

The finely ground active ingredient is uniformly applied, in a mixer, to the kaolin moistened with polyethylene glycol. Non-dusty coated granulates are obtained in this manner.

| (10) Suspension concentrate | |
|---|---|
| active ingredient | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

EXAMPLE 1

(a) Preparation of N'-[N-(4-methylbenzoyl)-N-methylamido]-sulfenyl-N'-methylcarbamoylfluoride 15.7 g of HF are introduced at −50° C. into 200 ml of toluene (in a polyethylene apparatus). Then 46.7 ml of N-methylisocyanate are added dropwise at −50° C. The mixture is then stirred for 2 hours at −30° to −50° C. and subsequently diluted with toluene. At −10° C. the dropwise addition is made firstly of 145 g of 4-methylbenzoylamidomethylsulfenyl chloride and then, over 30 minutes, of 108.5 ml of triethylamine. The reaction mixture is stirred for 18 hours at 20° C. and for 6 hours at 50° C., then cooled and filtered with suction. The filtrate is concentrated. Recrystallisation of the crude product from methylene chloride/hexane (1:1) yields the compound of the formula

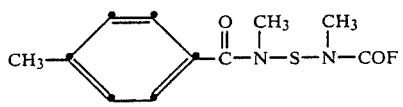

with a melting point of 66°–67° C.

The following compounds are also prepared in analogous manner:

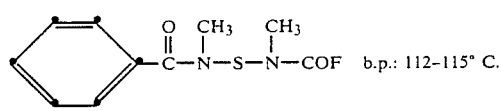 b.p.: 112–115° C.

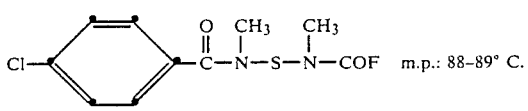 m.p.: 88–89° C.

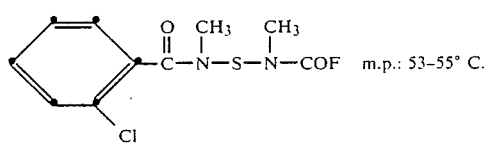 m.p.: 53–55° C.

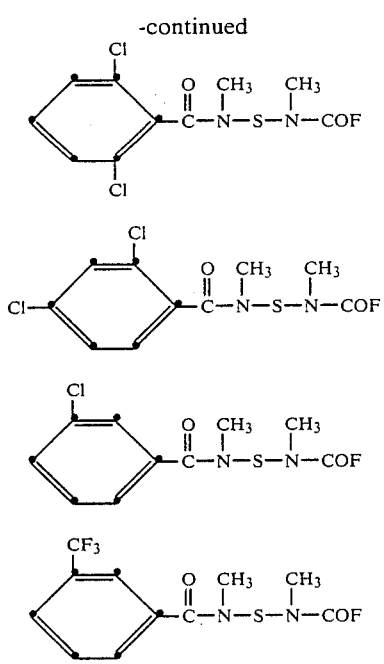

(b) Preparation of N'-[N-(4-methylbenzoyl)-N-methylamido)-sulfenyl]-[(N'-methylcarbamoyl)oxy]thioacetimidate 6.3 g of 1-methylmercaptoacetaloxime and 15.4 g of N'-[N-(4-methylbenzoyl)-N-methylamidosulfenyl]-N'-methylcarbamoylfluoride are dissolved in 50 ml of methylene chloride. With stirring, 11.05 g of triethylamine are added dropwise to this solution. The reaction mixture is stirred for 16 hours at 20° C. and for 2 hours at 45° C. The solvent is distilled off and the crude product is recrystallised from a 1:1 mixture of methylene chloride and hexane, affording the compound of the formula

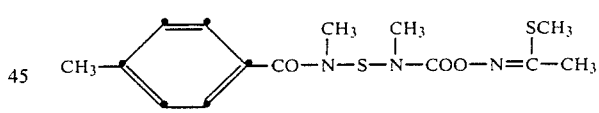

with a melting point of 118°–121° C.

The following compounds are also prepared in analogous manner:

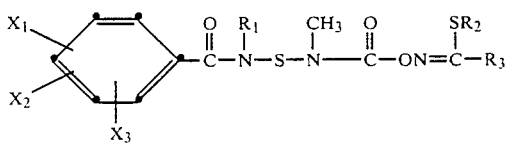

| $X_1$ | $X_2$ | $X_3$ | $R_1$ | $R_2$ | $R_3$ | Physical data |
|---|---|---|---|---|---|---|
| H | H | H | $CH_3$ | $CH_3$ | $CH_3$ | m.p.: 98–102° C. |
| H | H | H | $CH_3$ | $C_2H_5$ | $CH_3$ | $n_D^{20°} = 1.5525$ |
| H | H | H | $CH_3$ | $C_3H_{7(i)}$ | $CH_3$ | m.p.: 74–77° C. |
| H | H | H | $CH_3$ | $C_3H_{7(n)}$ | $CH_3$ | m.p.: 86–90° C. |
| H | H | H | $CH_3$ | $CH_3$ | $-CON(CH_3)_2$ | m.p.: 145–147° C. |
| 4-Cl | H | H | $CH_3$ | $CH_3$ | $CH_3$ | m.p.: 117–120° C. |
| 2-Cl | H | H | $CH_3$ | $CH_3$ | $CH_3$ | m.p.: 136–137° C. |
| 4-Cl | H | H | $CH_3$ | $C_2H_5$ | $CH_3$ | m.p.: 56–58° C. |
| 2-Cl | H | H | $CH_3$ | $C_2H_5$ | $CH_3$ | m.p.: 112–114° C. |

-continued $$\underset{X_3}{\underset{X_2}{X_1}}\diagdown\diagup\overset{O}{\underset{\|}{C}}-\overset{R_1}{\underset{|}{N}}-S-\overset{CH_3}{\underset{|}{N}}-\overset{O}{\underset{\|}{C}}-ON=\overset{SR_2}{\underset{|}{C}}-R_3$$

| $X_1$ | $X_2$ | $X_3$ | $R_1$ | $R_2$ | $R_3$ | Physical data |
|---|---|---|---|---|---|---|
| 4-$CH_3$ | H | H | $CH_3$ | $C_2H_5$ | $CH_3$ | m.p.: 83–85° C. |
| 4-Cl | H | H | $CH_3$ | $CH_3$ | —$CON(CH_3)_2$ | m.p.: 137–139° C. |
| 2-Cl | H | H | $CH_3$ | $CH_3$ | —$CON(CH_3)_2$ | m.p.: 138–139° C. |
| 4-$CH_3$ | H | H | $CH_3$ | $CH_3$ | —$CON(CH_3)_2$ | m.p.: 106–108° C. |
| 3-Cl | H | H | $CH_3$ | $CH_3$ | $CH_3$ | resin |
| 3-$CF_3$ | H | H | $CH_3$ | $CH_3$ | $CH_3$ | resin |
| 2-Cl | 4-Cl | H | $CH_3$ | $CH_3$ | $CH_3$ | m.p.: 135° C. |
| 2-Cl | 6-Cl | H | $CH_3$ | $CH_3$ | $CH_3$ | resin |
| 4-$CH_3$ | H | H | $C_3H_{7(i)}$ | $CH_3$ | $CH_3$ | m.p.: 101–103° C. |
| H | H | H | $C_4H_{9(n)}$ | $CH_3$ | $CH_3$ | resin |
| H | H | H | $C_6H_{13(n)}$ | $CH_3$ | $CH_3$ | resin |
| 3-$CF_3$ | H | H | $CH_3$ | $CH_3$ | —$CON(CH_3)_2$ | resin |

BIOLOGICAL EXAMPLES

EXAMPLE 2

Insecticidal stomach poison action against *Spodoptera littoralis* and *Heliothis virescens*

Cotton plants are sprayed with a solution containing 50, 100, 200 or 400 ppm of the compound to be tested. After the coating has dried, the plants are populated with larvae of the species *Spodoptera littoralis* (L3-stage) or *Heliothis virescens* (L3-stage). Two plants are used for each test compound and test species. A mortality count is made after 2, 4, 24 and 48 hours. The test is carried out at 28° C. and 60% relative humidity.

Within the above concentration limits, the compounds of Example 1 effect 100% kill of larvae of the species *Spodoptera littoralis* and *Heliothis virescens*.

EXAMPLE 3

Insecticidal contact action against *Myzus persicae*

Before the start of the test, bean plants (*Vicia faba*) reared in water are each populated with about 200 insects of the species *Myzus persicae*. The treated plants are sprayed 3 days later dripping wet from a distance of 30 cm with a solution containing 10 or 1 ppm of the compound to be tested. Two plants are used for each test compound at its given concentration and a mortality count is made after a further 24 hours.

Within the above concentration limits, the compounds of Example 1 effect 100% kill of insects of the species *Myzus persicae*.

EXAMPLE 4

Systemic insecticidal action against *Aphis craccivora*

Bean plants which have grown roots are transplanted into pots containing 600 ccm of soil and then 50 ml of a solution containing 25 ppm, 5 ppm or 1 ppm of the compound to be tested are poured direct onto the soil.

After 24 hours the parts of the plants above the soil are populated with lice of the species *Aphis craccivora* and a plastic cylinder is then slipped over the plants to protect the lice from any possible contact with the test substance either directly or via the gas phase.

A mortality count is made 24 and 48 hours respectively after the start of the test. Two plants, each in a separate pot, are used per concentration of test substance. The test is carried out at 25° C. and 70% relative humidity.

Within the given concentration limits, the compounds of Example 1 have a 100% systemic action against insects of the species *Aphis craccivora*.

What is claimed is:

1. A compound of the formula

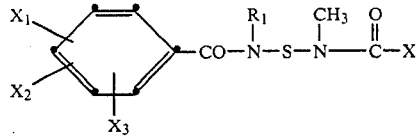

wherein $R_1$ is $C_1$–$C_{10}$ alkyl, X is fluorine or chlorine, and each of $X_1$, $X_2$ and $X_3$ is hydrogen, halogen, $C_1$–$C_4$ alkyl or $C_1$–$C_4$ haloalkyl.

2. A compound according to claim 1 in which X is fluorine.

* * * * *